(12) United States Patent
Baust et al.

(10) Patent No.: US 6,632,666 B2
(45) Date of Patent: Oct. 14, 2003

(54) NORMOTHERMIC, HYPOTHERMIC AND CRYOPRESERVATION MAINTENANCE AND STORAGE OF CELLS, TISSUES AND ORGANS IN GEL-BASED MEDIA

(75) Inventors: John M. Baust, Vestal, NY (US); Robert Van Buskirk, Apalachin, NY (US); John G. Baust, Candor, NY (US)

(73) Assignee: BioLife Solutions, Inc., Binghamton, NY (US)

( * ) Notice: Subject to any disclaimer, the term of this patent is extended or adjusted under 35 U.S.C. 154(b) by 39 days.

(21) Appl. No.: 09/757,694

(22) Filed: Jan. 11, 2001

(65) Prior Publication Data

US 2001/0049140 A1 Dec. 6, 2001

Related U.S. Application Data

(60) Provisional application No. 60/176,009, filed on Jan. 14, 2000.

(51) Int. Cl.[7] ............................. C12N 1/00; C12N 1/04; C12N 5/08
(52) U.S. Cl. ....................... 435/374; 435/243; 435/260; 435/366; 435/431
(58) Field of Search ................................. 435/243, 404, 435/431, 325, 326, 363, 366, 374, 397, 410, 420, 257.1, 260

(56) References Cited

U.S. PATENT DOCUMENTS

| | | | | |
|---|---|---|---|---|
| 4,774,093 A | * | 9/1988 | Provonchee et al. | 424/493 |
| 4,840,891 A | | 6/1989 | van Blerkom | 435/2 |
| 5,635,344 A | | 6/1997 | Garcia et al. | 435/1.1 |

FOREIGN PATENT DOCUMENTS

| FR | 2600671 | 12/1987 |
|---|---|---|
| WO | WO 92/08347 | 5/1992 |
| WO | WO 96/25848 | 8/1996 |
| WO | WO 00/53008 | 9/2000 |

OTHER PUBLICATIONS

Mathew et al., "Vitamin E and EDTA Improve the Efficacy of Hypothermosol—Implication of Apoptosis," Chemical Abstracts Database, Accession No. 132:20699 CA, XP002169438 and Invitro Mol. Toxicol., vol. 12, No. 3 (1999), pp. 163–172.

"Treatment of Cultured Skins for Preservation or Transportation . . . ,"Database WPI Section Ch, Week 199936, Derwent Publications Ltd., London, GB; Class 804, AN 1996–133411, XP002169439 and JP 02 928727 B (Gunze KK), (Aug. 3, 1999) Abstract.

"Transportation of Animal Cells Esp. Prim. Cultured Hepatocytes . . . ," Database WPI Section Ch, Week 199612, Derwent Publications Ltd., London, GB, Class 804, AN 1996–110267, XP002169440 and JP 08 009966 A (?Sumitomo Bakelite Co. Ltd.), (Jan. 16, 1996) Abstract.

* cited by examiner

*Primary Examiner*—David M. Naff
*Assistant Examiner*—Deborah K Ware
(74) *Attorney, Agent, or Firm*—Anthony L. Miele; Palmer & Dodge, LLP

(57) ABSTRACT

Gel-based medium compositions and a method of use thereof in normothermic, hypothermic or cryopreservative storage and transport of cell samples are described. These gel-based compositions contain a cell maintenance and preservation medium together with a gelling agent. Such gel-based medium compositions protect various cell samples, such as animal or plant organs, tissues and cells, from the mechanical, physiological and biochemical stresses inherently associated with liquid preservation techniques.

6 Claims, 8 Drawing Sheets

NORMOTHERMIC, HYPOTHERMIC AND CRYOPRESERVATION MAINTENANCE AND STORAGE OF CELLS, TISSUES AND ORGANS IN GEL-BASED MEDIA

This application claims the benefit of U.S. Provisional Application No. 60/176,009, filed Jan. 14, 2000.

BACKGROUND OF THE INVENTION

1. Field of the Invention

The invention relates to gel-based compositions for normothermic, hypothermic and cryopreservative transport or storage of plant tissues or cells and animal organs, tissues or cells, the gel-based compositions comprising a cell maintenance and preservation medium and a gelling agent.

2. Description of Related Art

Today, limited normothermic, hypothermic and cryopreservative maintenance and storage of plant or mammalian cells, tissues and organs (biologics) is accomplished in liquid media. Success is limited, in part, due to damage that occurs during shipment (transport), most often associated with mechanical trauma.

Preservation and transport (herein referred to as preservation) of biologics (cells, tissues, and organs) has traditionally been achieved through "suspension" in a liquid preservation medium. These media include, but are not limited to, simple saline solution, cell culture media, and preservation solutions such as University of Wisconsin (UW) solution (VIASPAN®), EURO-COLLINS®, and HYPOTHERMOSOL® (Bio Life Solutions, Inc., Ewing, N.J., USA). Inherent in this liquid preservation approach is that the liquid environment confers no physical support network for the biologic during preservation and transport. Due to this lack of physical support upon preservation, biologics are exposed to numerous physical stresses during storage and shipment. These stresses include, but are not limited to, sedimentation, mechanical "jarring", compaction in a liquid column, shaking, vibration, shearing forces, ice damage, and the like. As a result of these mechanical stresses plus additional biochemical stresses inherently associated with biologic preservation in liquid, a significant level of cellular death is initiated during and following the preservation interval. Consequently, failure of the biologic ensues due to this preservation-initiated cell death.

SUMMARY OF THE INVENTION

The invention relates to gel-based medium compositions for normothermic, hypothermic or cryopreservative transport and/or storage of plant tissues or cells and animal organs, tissues or cells, the gel-based compositions comprising a cell maintenance and preservation medium and a gelling agent. In particular, mammalian samples, such as human and animal organs, tissues and cells, may be preserved in the inventive gel-based media compositions.

In a preferred embodiment, the cell maintenance and preservation medium is liquid.

In another embodiment, the gel-based medium compositions comprise:

(a) one or more electrolytes selected from the group consisting of potassium ions at a concentration ranging from about 10–145 mM, sodium ions ranging from about 10–120 mM, magnesium ions ranging from about 0.1–10 mM, and calcium ions ranging from about 0.01–1.0 mM;

(b) a macromolecular oncotic agent having a size sufficiently large to limit escape from the circulation system and effective to maintain oncotic pressure equivalent to that of blood plasma and selected from the group consisting of human serum albumin, polysaccharide and colloidal starch;

(c) a biological pH buffer effective under physiological and hypothermic conditions;

(d) a nutritive effective amount of at least one simple sugar;

(e) an impermeant and hydroxyl radical scavenging effective amount of mannitol;

(f) an impermeant anion impermeable to cell membranes and effective to counteract cell swelling during cold exposure, said impermeant ion being at least one member selected from the group consisting of lactobionate, gluconate, citrate and glycerophosphate-like compounds;

(g) a substrate effective for the regeneration of ATP, said substrate being at least one member selected from the group consisting of adenosine, fructose, ribose and adenine;

(h) at least one agent which regulates cellular levels of free radicals; and (i) at least one gelling agent.

Yet another embodiment of the invention is a method of storing cell samples in a gel-based medium composition, the method comprising:

warming a gel-based medium composition to melt a gelling agent contained therein;

suspending cell samples in a cell preservation solution without a gelling agent;

mixing the suspended cell samples with the warmed gel-based medium composition;

cooling the cell samples to a chilled or frozen state, thereby solidify the gelling agent; and transferring the chilled or frozen cell samples to a desired storage temperature.

Optionally, the chilled or frozen cell samples may be transported in the gelled state.

DETAILED DESCRIPTION OF THE PREFERRED EMBODIMENTS

Figure 1:
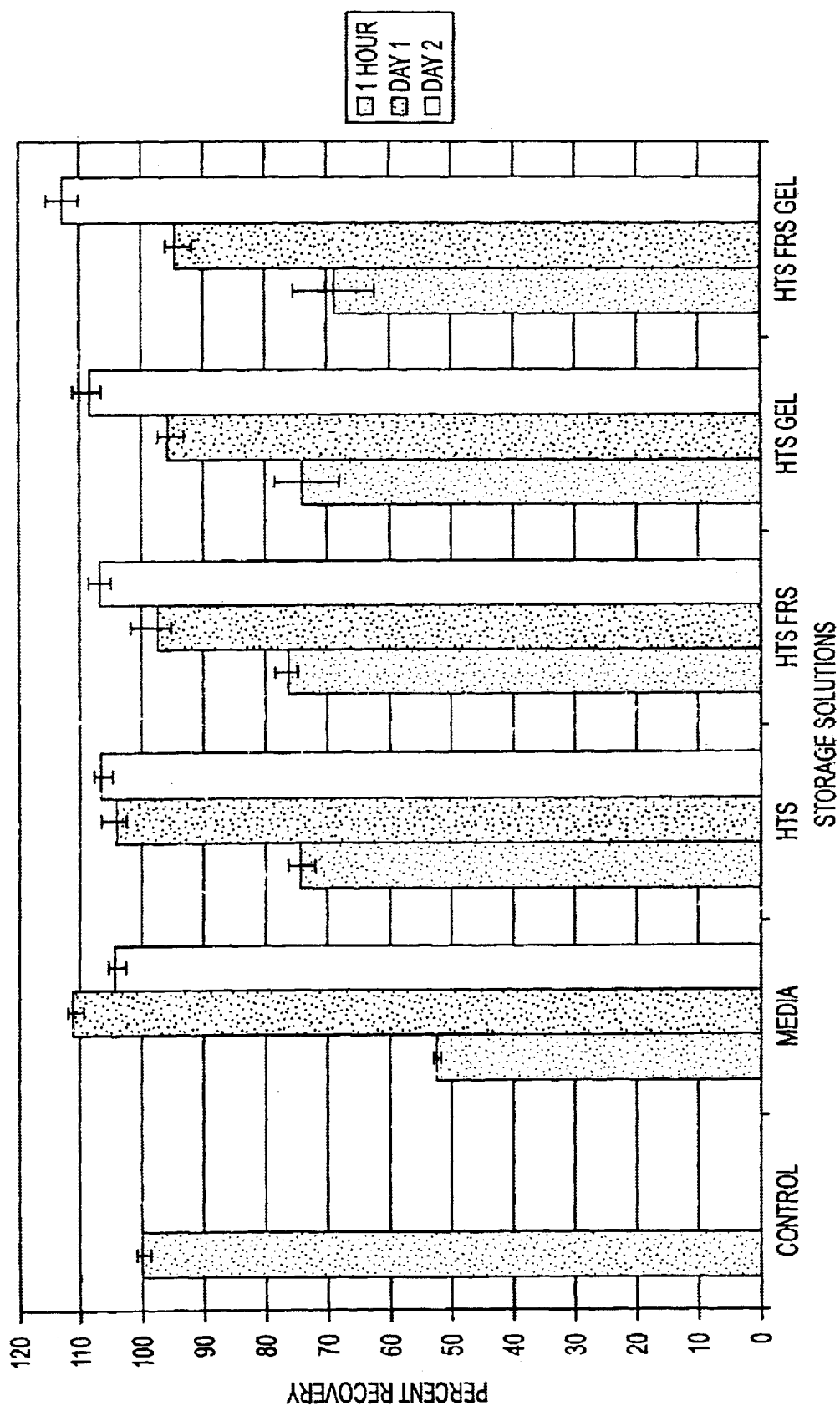
FIG. 1 graphically depicts post-storage recovery of MDCK (Madin Darby Canine Kidney) cells stored as monolayers in culture plates at 4° C. for 24 hours in liquid maintenance and preservation solutions (controls) (media, HTS, & HTS FRS) and in liquid maintenance and preservation solutions as gel formulations (HTS Gel & HTS FRS Gel)
Figure 2:
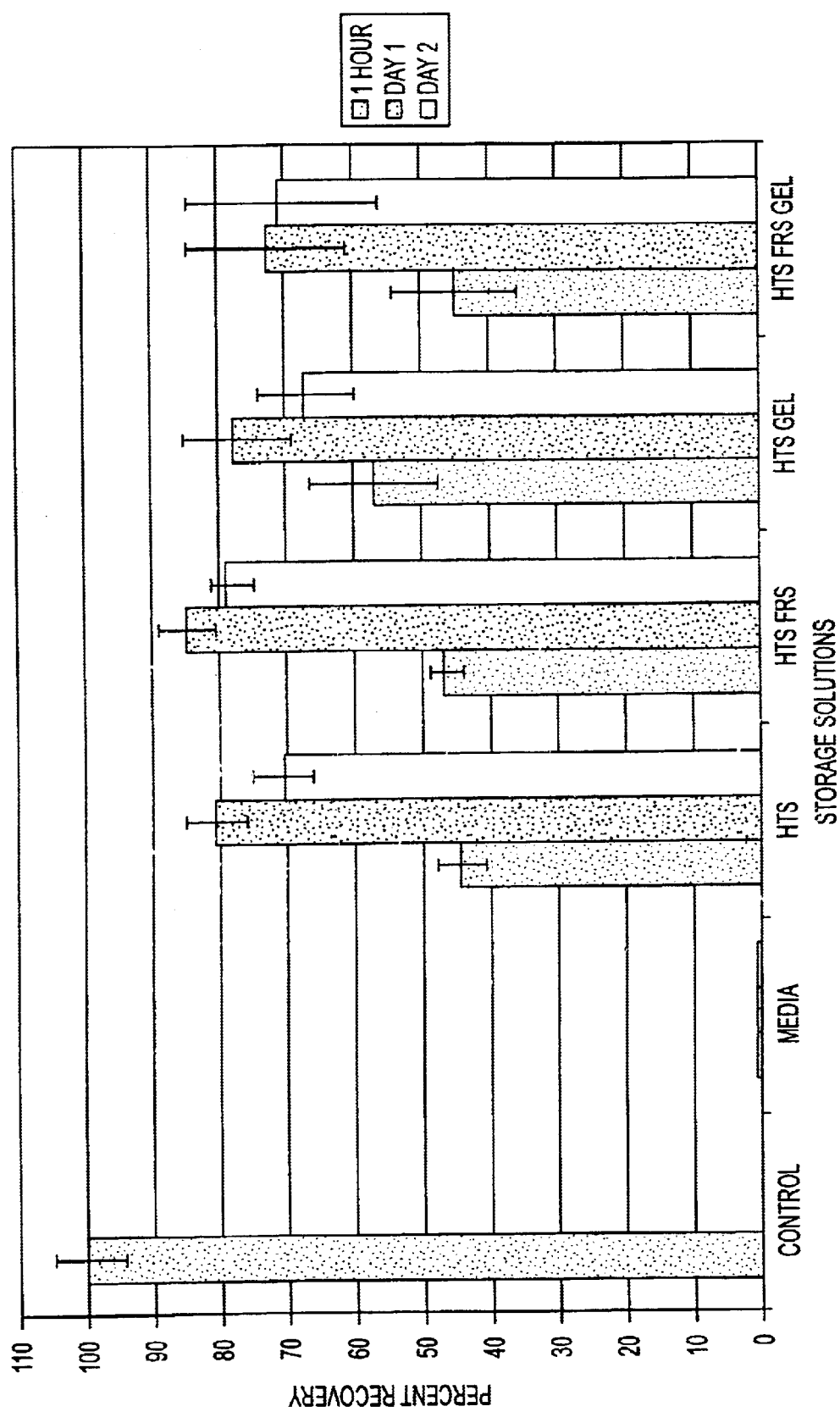
FIG. 2 graphically depicts post-storage recovery of MDCK cells stored as monolayers in culture plates at 4° C. for 3 days in liquid maintenance and preservation solutions (controls) (media, HTS, & HTS FRS) and in liquid maintenance and preservation solutions as gel formulations (HTS Gel & HTS FRS Gel).
Figure 3:
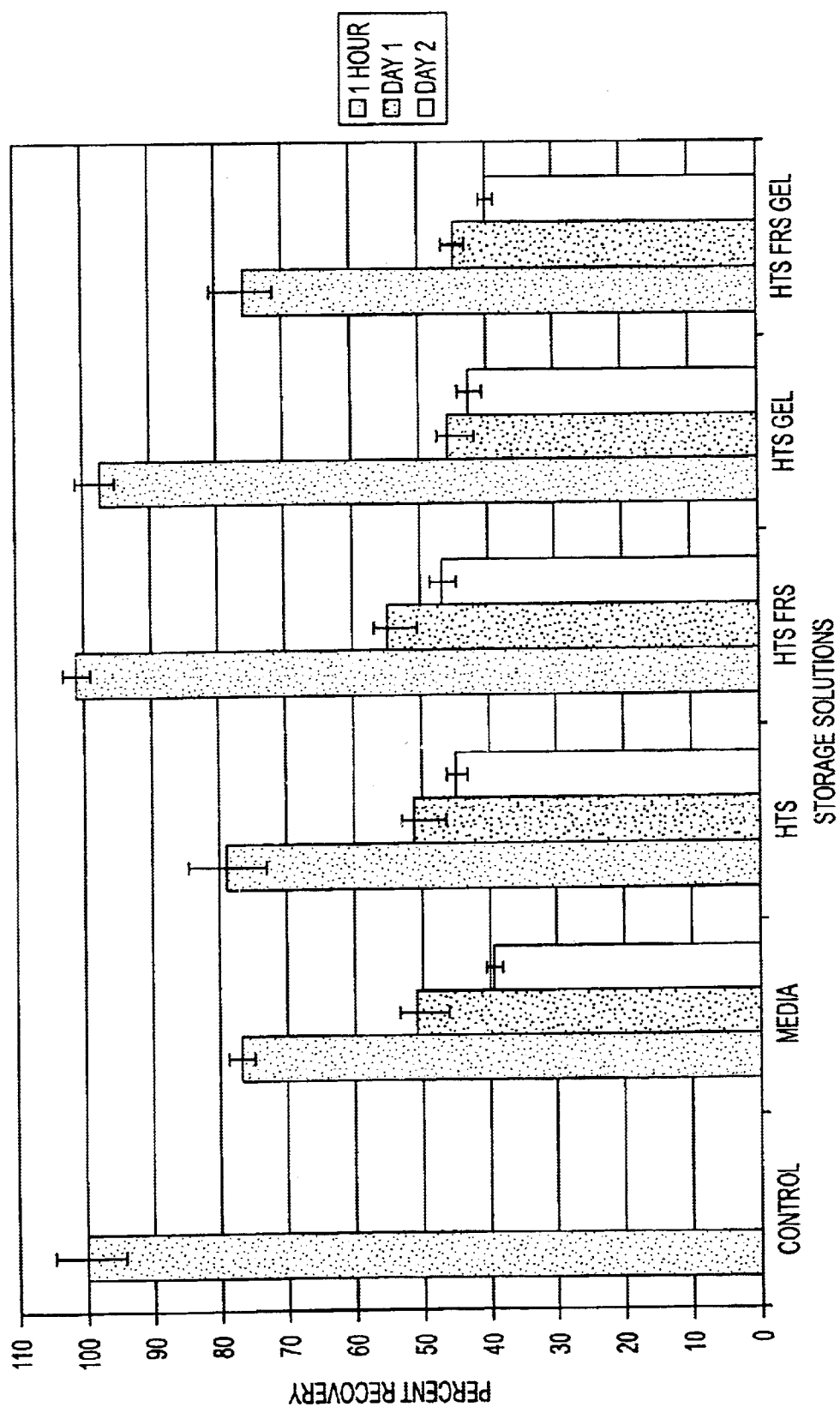
FIG. 3 graphically depicts post-storage recovery of MDCK cells stored in suspension in culture plates at 4° C. for 24 hours in liquid maintenance and preservation solutions (controls) (media, HTS, & HTS FRS) and in liquid maintenance and preservation solutions as gel formulations (HTS Gel & HTS FRS Gel)
Figure 4:
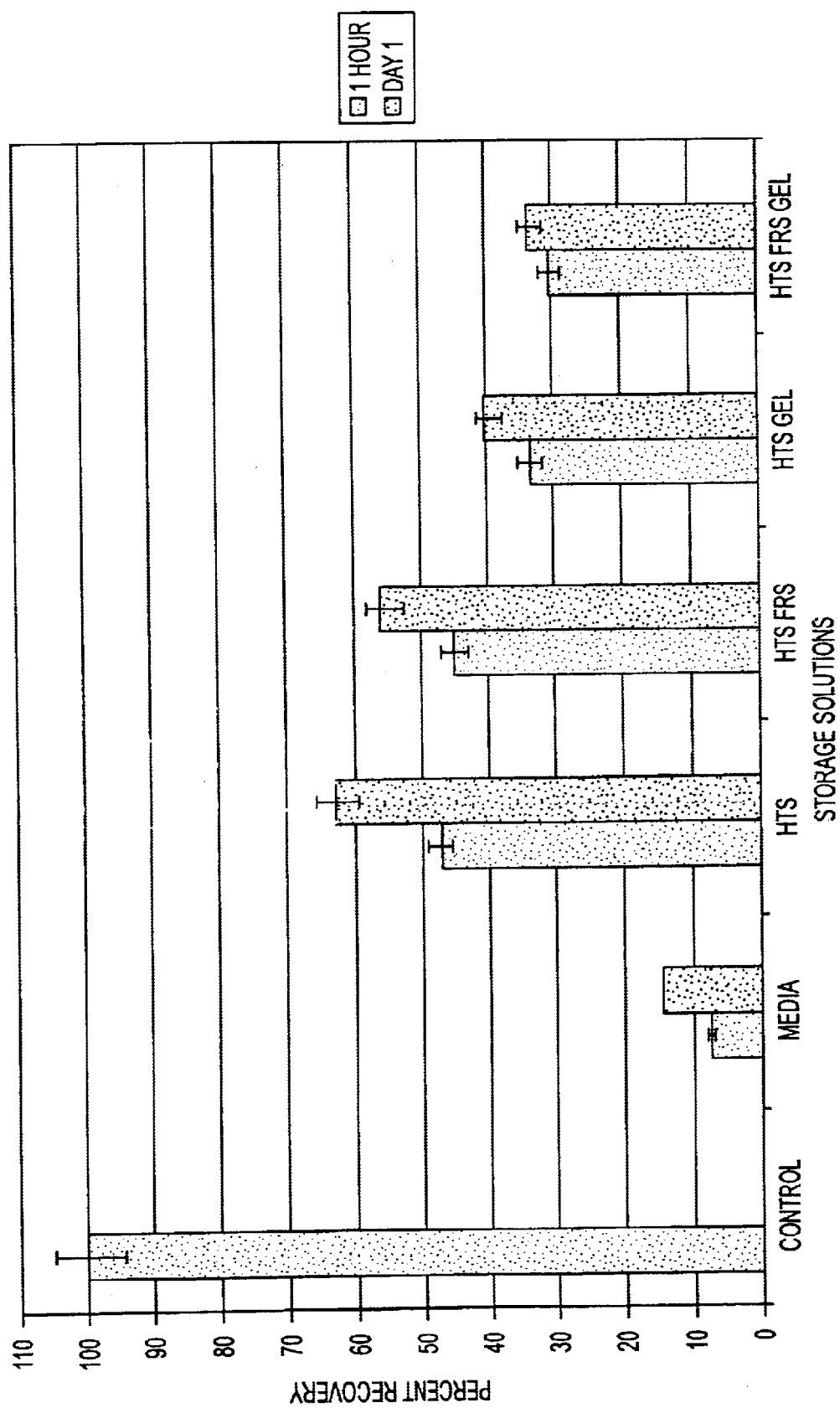
FIG. 4 graphically depicts post-storage recovery of MDCK cells stored in suspension in culture plates at 4° C. for 3 days in liquid maintenance and preservation solutions (controls) (media, HTS, & HTS FRS) and in liquid maintenance and preservation solutions as gel formulations (HTS Gel & HTS FRS Gel)
Figure 5:
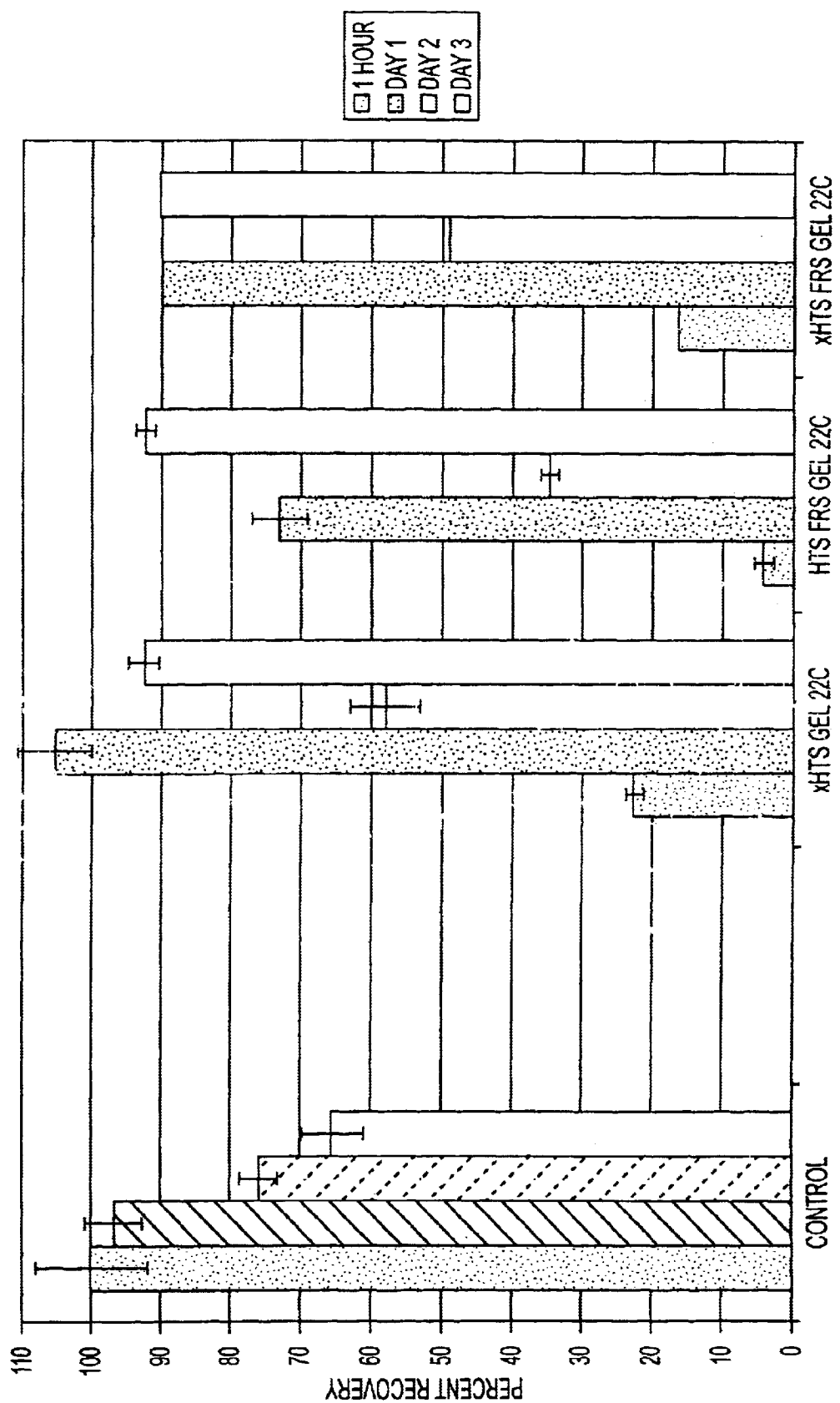
FIG. 5 graphically depicts post-storage recovery of human pancreatic Islets of Langerhans micro-organs stored in suspension in culture plates at 22° C. for 1 day in maintenance and preservation solutions as gel formulations.
Figure 6:
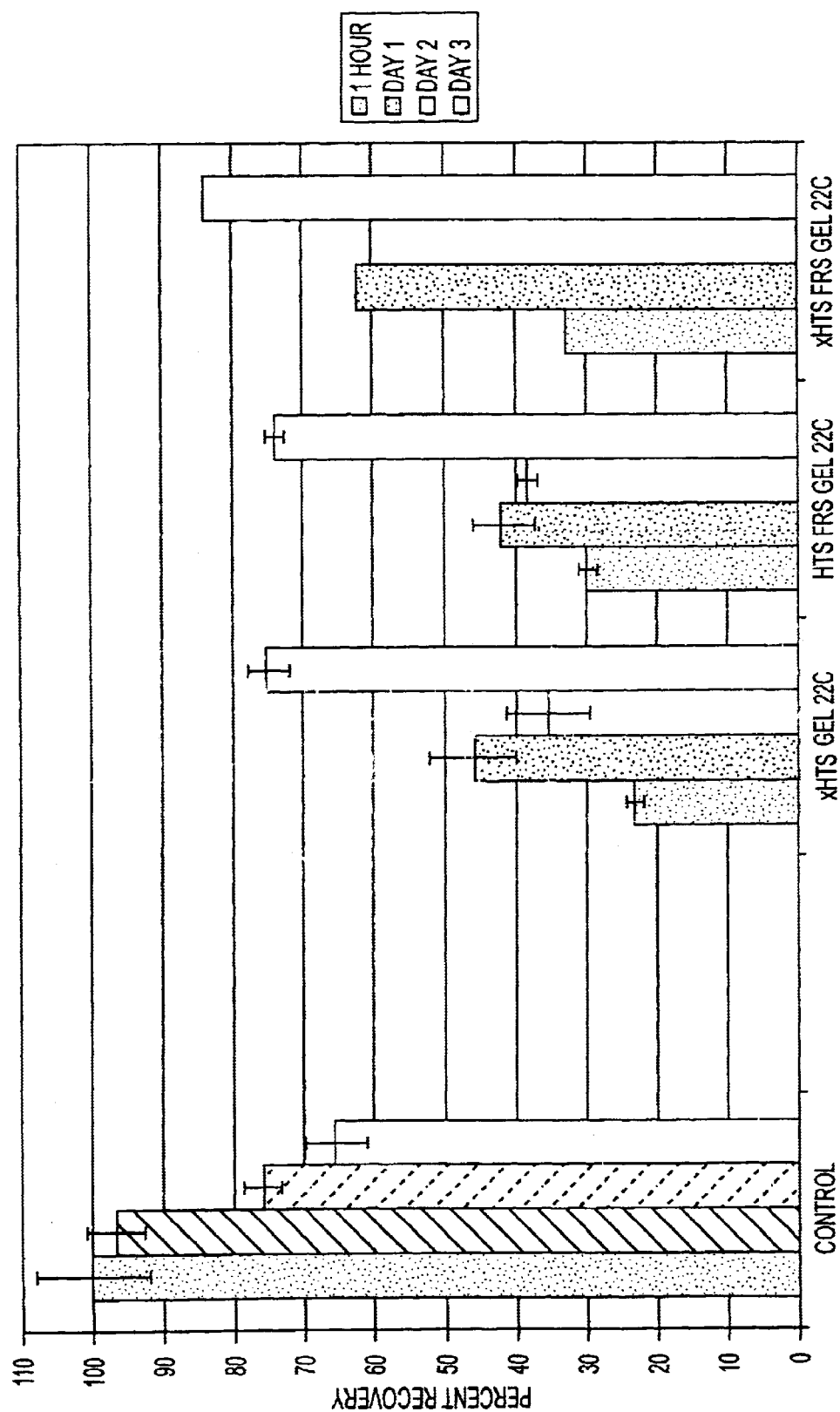
FIG. 6 graphically depicts post-storage recovery of human pancreatic Islets of Langerhans micro-organs stored in suspension in culture plates at 22° C. for 3 days in maintenance and preservation solutions as gel formulations.
Figure 7:
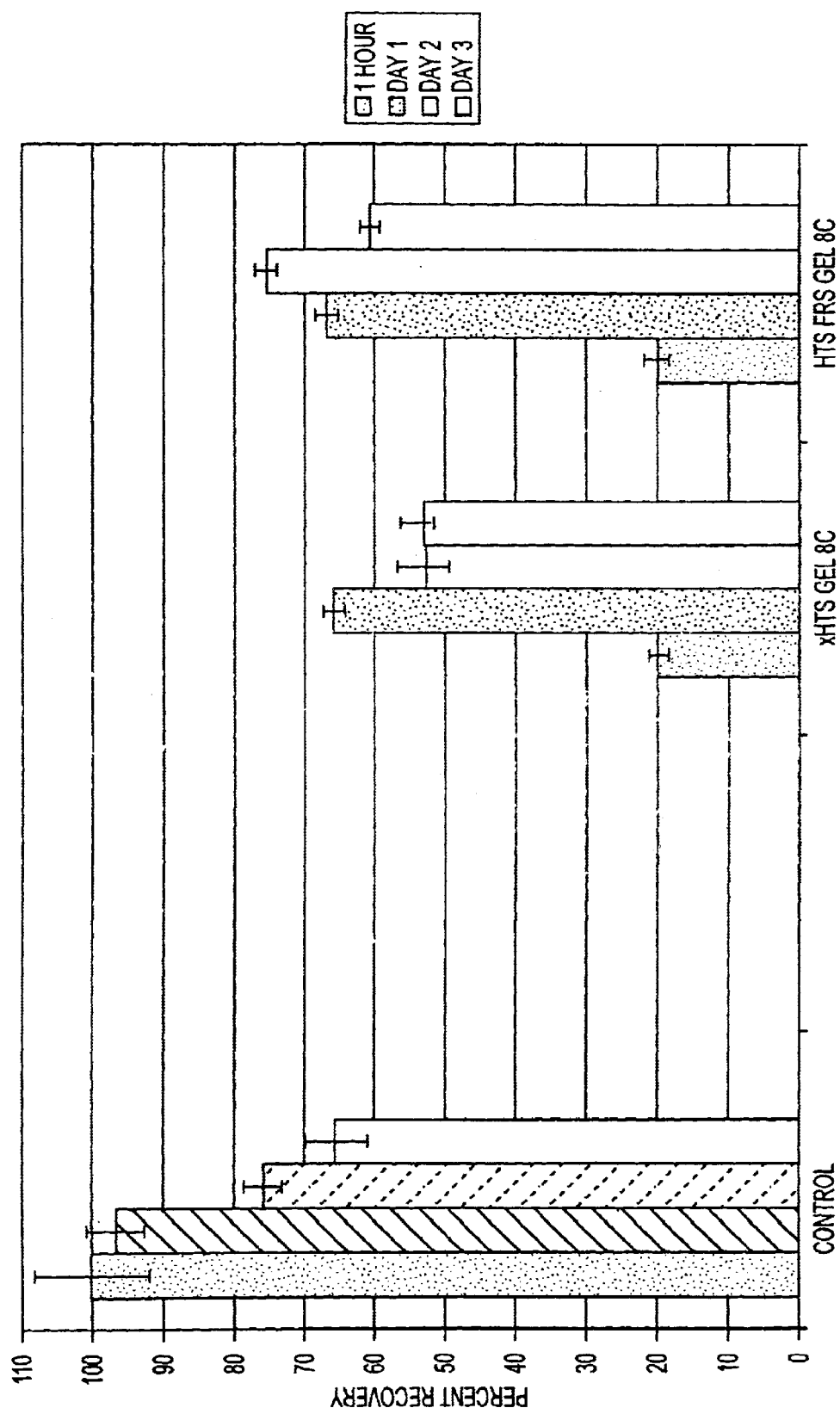
FIG. 7 graphically depicts post-storage recovery of human pancreatic Islets of Langerhans micro-organs stored in suspension in culture plates at 8° C. for 1 day in maintenance and preservation solutions as gel formulations.
Figure 8:
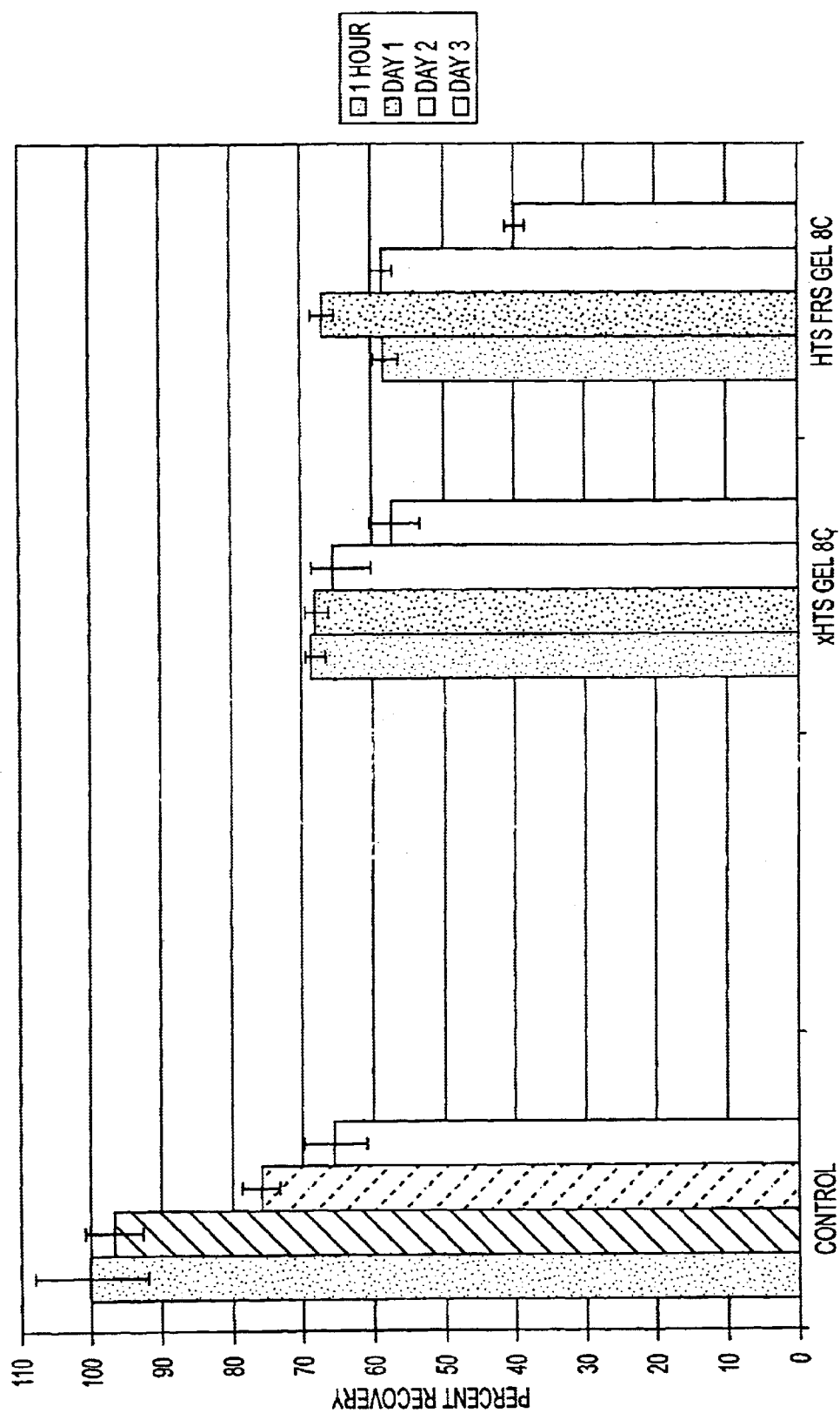
FIG. 8 graphically depicts post-storage recovery of human pancreatic Islets of Langerhans stored in suspension in culture plates at 8° C. for 3 days in maintenance and preservation solutions as gel formulations.

To reduce and even eliminate damage associated with mechanical factors arising from cell storage and transport, gel-based maintenance and preservation media have been developed to sustain biologics in supporting environments of various viscosity. The gel-based media are rigid or highly viscous at temperatures equal to or lower than 28° C. but liquid at 37° C. Liquid maintenance and preservation media (i.e., HYPOTHERMOSOL®, VIASPAN® (also called University of Wisconsin solution), EUROCOLLINS®, CARDISOL®, UNISOL®, tissue culture media, etc.) are converted to a gel of appropriate viscosity necessary to match cell, tissue or organ type with either animal or plant derived gelling agents (1–2% by volume). Suitable combinations of such liquid maintenance and preservation solutions may be used if desired. A preferred organ preservation solution is HYPOTHERMOSOL®, which is composed of:

(a) one or more electrolytes selected from the group consisting of potassium ions at a concentration ranging from about 10–145 mM, sodium ions ranging from about 10–120 mM, magnesium ions ranging from about 0.1–10 mM, and calcium ions ranging from about 0.01–1.0 mM;
(b) a macromolecular oncotic agent having a size sufficiently large to limit escape from the circulation system and effective to maintain oncotic pressure equivalent to that of blood plasma and selected from the group consisting of human serum albumin, polysaccharide and colloidal starch;
(c) a biological pH buffer effective under physiological and hypothermic conditions;
(d) a nutritive effective amount of at least one simple sugar;
(e) an impermeant and hydroxyl radical scavenging effective amount of mannitol;
(f) an impermeant anion impermeable to cell membranes and effective to counteract cell swelling during cold exposure, said impermeant ion being at least one member selected from the group consisting of lactobionate, gluconate, citrate and glycerophosphate-like compounds;
(g) a substrate effective for the regeneration of ATP, said substrate being at least one member selected from the group consisting of adenosine, fructose, ribose and adenine; and
(h) at least one agent which regulates cellular levels of free radicals.

By adjusting the formulation of 1) the carrier medium, in particular, a cell maintenance and preservation solution, 2) gel-type and 3) gel concentration, an appropriate long-term (up to two weeks) shipping environment has been produced, and is commercially known as GELSTOR™ (Biolife Solutions, Inc., Ewing, N.J., USA). Procedurally, a biologic of choice is exposed to liquefied gel at 37° C., and thereafter cooled to a desired preservation temperature for maintenance and shipment. Upon arrival or point-of-use, the gel is warmed to 37° C. whereupon it liquefies, and may be decanted. The biologic may then be rinsed with an appropriate medium and is ready for use.

The gel-based preservation and maintenance technology disclosed herein has been developed to provide a semi-solid preservation matrix that facilitates protection of various cells from mechanical stresses associated with biologic preservation and transport. In addition to physical protection, gel-based preservation media provide physiological and biochemical protection during the storage and transport of cells, organs and tissues.

A variety of animal and plant cells may be stored and transported in gel-based media, including human cells and animals cells from numerous tissue sources, including tumor cells, cells from the liver, kidney, central nervous system, epidermal keratinocytes, endothelial cells, stem cells, white blood cells, fibroblasts, pancreatic islet cells, cardiac and skeletal muscle cells, sperm, egg, satellite cells and the like. Fetal, neonatal, juvenile and adult cells, tissues and organs all benefit from the protective aspects of the inventive gel-based carrier media. In particular, cells from younger sources are highly sensitive to the mechanical stresses of preservation and transport, and thus are ideal candidates for the mechanically protective aspects of a gel-based preservation medium. Conversely, cells from older sources are highly susceptible to damage from oxidative stresses incurred during preservation and transport, meaning these cells particularly benefit from the physiological and biochemical protection afforded by gel-based preservation media.

Cell lines and tissues from which cell lines are to be developed are suitable for storage and/or preservation in gel-based media. Likewise, organs and tissues from donor animals destined for transplantation into other animals, including humans, will have greater viability upon storage and transport in gel-based media. Plant cells and tissues, such as those from transformed or transgenic sources may be stored and/or transported in gel-based media. Likewise, tissue grafts of plants are suitable samples for preservation and, if desired, transport in a gel-based medium. Microbial and fungal cells would also benefit form storage and transport in a gel-based preservation media. For example, microbial systems used in environmental remediation, such as bacterially-mediated oil degradation or sewage treatment, may be successfully transported to a point of use in a gel-based preservation medium.

Traditionally, preservation and transport of single cells has relied on suspension of cells in a liquid-based medium. Such liquid-based preservation regimes result in the settling of cells to the bottom of the preservation container. This settling causes an inhomogeneous distribution of the cells in the medium resulting inefficient exposure of the cells to the preservation solution, as well as the exposure of the cells to mechanical stresses of "jarring and shearing" experienced during shipment. Accordingly, gelled preservation solutions permit maintenance of cells in suspension during periods of preservation. This maintenance of cellular suspension eliminates cell sedimentation and reduces mechanical stresses experienced by the cells subjected to storage and/or transport conditions. Additionally, the composition of the inventive gelled preservation medium is designed to provide a biochemical environment beneficial to cellular preservation. This protective environment is facilitated through the incorporation of an organ preservation solution as the principal diluent in which the gellation component of the medium is mixed.

Cellular monolayers are sheets of cells one to a few cell layers thick that are grown on an inert matrices in vitro. These monolayers are typically preserved in liquid based preservation mediums. Due to preservation in liquid-based media, monolayer separation from the growth matrix occurs during preservation. This separation results in the dissembling of the system and ultimately failure caused by the preservation process. Preservation of cellular monolayers using the inventive gelled medium prevents cell-matrix separation during the preservation interval. Additionally, gelled media provide the same preservation benefits to cellular monolayers as is conferred upon cellular suspensions.

Biologic tissues are multi-layered cellular constructs that interact to perform a particular function. The complexity of tissues ranges from engineered tissue constructs consisting of a single cell type (i.e. EPIDERM™ MatTech, Ashland, Mass., USA) to human skin grafts, to "micro-organs" (i.e. pancreatic islets), to whole human organs (i.e. kidneys, livers, etc.). Preservation of these cell systems, as with single cells and monolayers, is typically performed utilizing liquid preservation media. Due to the complex nature of tissues, the shortcomings of liquid-based preservation technologies include those associated with cell and monolayer preservation, along with the inability to maintain the more intricate cell—cell interactions that are stressed during periods of preservation.

The inventive gelled preservation media enables preservation of tissue in a semi-solid preservation matrix keeping the tissue structurally intact while affording the same protective benefits to the tissue as is conferred to individual cells and cell monolayers. Specifically, the reduction in the external mechanical shipping forces experienced by the tissues shipped in the inventive gel medium markedly improves tissue viability following preservation. For example, pancreatic islet cells preserved in a medium comprising gelatin and HYPOTHERMOSOL® were afforded significant improvement of islet integrity and functionality following preservation.

Types of gellation material suitable for use in a gelled cell preservation medium include gelatin, carrageenan, agarose, collagen, plant-based gelling agents, combinations thereof and the like. Plant-based gelling agents include gels produced from the roots, stems, tubers, fruit and seeds of plants.

The invention is further described in the following non-limiting examples.

EXAMPLES

Example 1

Gel-Based Medium Preparation

Calculations are first performed to determine the necessary volume of gel-based medium for a given storage or transport need. The desired gel concentration must be established. Typically, a standard concentration of 2% is used, although this concentration may vary depending upon the characteristics of the biologic being preserved. A stock solution of gel-based medium was then prepared (standard= 14%) in a sterile environment. The volume of stock solution needed was determined and the mass of the appropriate amount of gelatin powder (Sigma Chemicals, St. Louis, Mo., USA) was ascertained. The appropriate volume of organ preservation solution (HYPOTHERMOSOL®, or "HTS") was measured and combined via agitation with the gelatin powder. In this instance, the stock solution was mixed by swirling the container having the HTS and gelatin, although any suitable means of agitation may be employed. The stock solution of gel-based medium was then warmed in a 40° C. water bath for 15–20 min with repeated swirling solution (once per minute) to dissolve the gelatin. A 2% solution of gel-based medium was then prepared from this stock solution. The desired volume depended upon the quantity of cells to be preserved. For example, for 100 ml of the 2% solution of gel-based medium, 14 ml of 14% stock solution of gel-based medium was combined with 86 ml of an HTS-Free Radical System (FRS) solution. Aliquots of this 2% solution of gel-based medium were dispensed into 15 ml centrifuge tubes at 10 ml per tube, which were stored at 4° C. until used.

Example 2

Gel-Based Medium Storage Protocol

Aliquots of previously prepared 2% gel-based medium were removed from 4° C. storage and placed into a 37° C. water bath for 15 minutes to melt the gelatin contained therein. While the gel-based medium was warming, samples destined for preservation therein were prepared in a sterile environment. The desired number of cells to be preserved were transferred into a clean centrifuge tube and were gently centrifuged to pellet cells. Typically, centrifugation at 500×g for 6 min is sufficient to generate a cell pellet from which a supernatant can be decanted. Pelleted cells were then suspended in 0.5–1.0 ml of HTS-FRS solution without gelatin, which is an appropriate volume for preservation in 2% gel-based HTS-FRS medium. The warmed 2% gel-based medium, now in solution form, was removed from the water bath and the suspended cells were pipetted into the warmed medium in a sterile cell culture environment. After tightly securing lids onto the sample storage tubes, the tubes were immediately placed into an ice-water bath for 5 minutes to allow for rapid solidification of the gel-based medium solution. A 2% gel-based medium solution will solidify around room temperature in approximately 30 min, and chilling was used to accelerate the solidification. Chilled sample tubes were then transferred to a desired storage temperature.

Samples prepared in this manner can be stored for any desired time period at appropriate temperatures. For example, cells may be stored for less than 24 hours or for as long as about three days. Storage temperatures can range, for example, from about −196° C. to about +30° C.

Temperatures are considered "normothermic" in a range between 31° C.–37° C. Temperatures are considered "hypothermic" in a range between 0° C. and 30° C. Cryopreservation generally occurs at temperature below 0° C., and may be effected using a combination of a gel-based media with cryopreservants.

Sample tubes are removed from storage when the cells contained therein are to be used. Accordingly, the sample tubes is this instance were placed in a 37° C. water bath for 6–8 minutes to melt the gelled medium. However, the gelling agent can be formulated into a preservation medium such melting can occur at any desired temperature above or below 37° C. While samples were thawing, tubes were inverted every 30 seconds to maintain uniform temperature throughout the samples. Once the gelled medium containing sample cells melted, samples were immediately removed from the water bath. Cell samples were then gently centrifuged to form pellets, typically at 37° C. at 500×g for 6 min. Cell sensitivity to heat stress will delimit tolerable temperature ranges for gel melting for a given biologic. Centrifugation can be performed at room temperature, but the gel-based medium solution may partially resolidify at this temperature. Resolidification causes uncontrolled gel concentration within the cell pellet during centrifugation. For this reason centrifugation at temperatures between 30° C.–37° C. is preferred.

After centrifugation, the gel-based medium supernatant was decanted from the cell pellet, which was then suspended in 12 ml of an appropriate cell culture medium at 37° C. to wash residual gel solution from the cells. The samples were then gently centrifuged to pellet cells at 37° C., typically at 500×g for 6 min. The supernatant was decanted from the pelleted cells prior to resuspension to a desired cell density in an appropriate volume of cell culture media at 37° C. Suspended cells were then be transferred to cell culturing vessels at the density desired for growth.

While a preferred form of the invention has been herein described, a skilled artisan would understand that the present disclosure is by way of example and that variations are possible without departing from the subject matter described within the scope of the entire invention disclosed herein. All published materials cited herein are hereby incorporated in their entirety by reference.

What is claimed is:

1. A method for increasing a storage duration of a cell sample at frozen temperatures, the method comprising:

forming a cell pellet;

mixing the pellet with a cell preservation medium comprising a cryopreservant, said medium not containing a gelling agent;

adding a medium containing a gelling agent to the mixture of cells and cell preservation medium, the medium containing the gelling agent being in a liquid state when added;

reducing the temperature of the resulting mixture until the mixture gels; and storing the gelled mixture at a temperature below 0° C.

2. The method of claim 1 wherein the gelled mixture is stored at a temperature of below 0° C. to −196° C.

3. The method of claim 1 wherein the cell sample is obtained from a source selected from the group consisting of plants, animals, fungi and microbes.

4. The method of claim 1 wherein the source of the cell sample is a fetal, neonatal, juvenile or adult animal.

5. The method of claim 1 wherein the cell sample is a human cell sample.

6. The method of claim 1 wherein said cell preservation medium comprises one or more electrolytes selected from the group consisting of potassium ions at a concentration ranging from about 10–145 mM, sodium ions ranging from about 10–120 mM, magnesium ions ranging from about 0.1–10 mM, and calcium ions ranging from about 0.01–1.0 mM.

* * * * *